US012605286B2

(12) United States Patent 
Sinda et al.

(10) Patent No.: US 12,605,286 B2 
(45) Date of Patent: Apr. 21, 2026

(54) UMBILICAL CORD STUMP PROTECTOR

(71) Applicant: ASO LLC, Sarasota, FL (US)

(72) Inventors: Edmund A. Sinda, Sarasota, FL (US); Brooke A. Hagerty, Sarasota, FL (US); Mira Dosen, Sarasota, FL (US)

(73) Assignee: ASO LLC, Sarasota, FL (US)

( * ) Notice: Subject to any disclaimer, the term of this patent is extended or adjusted under 35 U.S.C. 154(b) by 0 days.

(21) Appl. No.: 17/588,842

(22) Filed: Jan. 31, 2022

(65) Prior Publication Data

US 2023/0240899 A1 Aug. 3, 2023

(51) Int. Cl. 
A61F 13/0206 (2024.01) 
A61F 13/00 (2024.01)

(52) U.S. Cl. 
CPC A61F 13/0206 (2013.01); *A61F 2013/00272* (2013.01)

(58) Field of Classification Search 
CPC .............. A61F 13/0203; A61F 13/0206; A61F 13/0246; A61F 13/148; A61F 13/493; A61F 2013/00165; A61F 2013/00272; A61F 2013/15032; A61F 2013/1504; A61F 2013/00182; A61F 2013/00846; A61F 15/008; A61F 2013/00387; A61F 2013/00395; A61F 2013/00574; A61F 2013/00578; A61F 13/069; A61F 13/14; A61J 13/00 
USPC ........................................................ 128/888 
See application file for complete search history.

(56) References Cited

U.S. PATENT DOCUMENTS

| | | | | |
|---|---|---|---|---|
| 4,212,296 A | * | 7/1980 | Schaar | A61F 13/063 602/42 |
| 4,846,829 A | * | 7/1989 | Lloyd | A61F 13/51401 604/389 |
| 5,170,781 A | * | 12/1992 | Loomis | A61F 13/0203 602/41 |
| 5,203,806 A | * | 4/1993 | Broida | A61F 13/45 604/338 |
| 5,681,579 A | * | 10/1997 | Freeman | A61F 13/023 602/44 |
| 6,096,943 A | * | 8/2000 | Maiwald | A61F 15/008 602/54 |

(Continued)

FOREIGN PATENT DOCUMENTS

| | | | | | |
|---|---|---|---|---|---|
| CN | 202426729 U | * | 9/2012 | | A61F 13/14 |
| WO | WO-2007044647 A2 | * | 4/2007 | | A61B 17/0057 |

OTHER PUBLICATIONS

Translation of CN-202426729-U (Year: 2012).*

*Primary Examiner* — Rachael E Bredefeld 
*Assistant Examiner* — Seth R. Brown 
(74) *Attorney, Agent, or Firm* — GrayRobinson, P.A.

(57) ABSTRACT

An infant umbilical cord stump protector includes a pad positionable proximal to the umbilical cord stump and a cover including fluid impermeable material over the pad. The fluid impermeable material has (i) an adhesive region that is adhereable to the infant about the umbilical cord stump, (ii) a deformable region, and (iii) a periphery about the deformable region. The deformable region has greater flexibility than the periphery in such a way that the cover can form a dome-like shape about the umbilical cord stump. The umbilical cord stump protector is used to protect the umbilical cord stump while it dries.

51 Claims, 9 Drawing Sheets

100

(56)  References Cited

U.S. PATENT DOCUMENTS

| | | | |
|---|---|---|---|
| 6,875,200 B1 * | 4/2005 | Ajagbe | A61F 13/148 |
| | | | 604/289 |
| 7,770,237 B1 | 8/2010 | Wright et al. | |
| 8,911,417 B2 | 12/2014 | Mundschau et al. | |
| D992,121 S | 7/2023 | Sinishtaj | |
| 2014/0060548 A1 * | 3/2014 | Check | A61F 15/008 |
| | | | 128/845 |
| 2014/0358058 A1 * | 12/2014 | Nelson | A61F 13/05 |
| | | | 602/42 |
| 2019/0030225 A1 * | 1/2019 | Lin | A61M 1/91 |
| 2019/0053962 A1 * | 2/2019 | Lavon | A61F 13/0246 |
| 2020/0046570 A1 * | 2/2020 | Sheridan | A61F 13/0233 |
| 2021/0393444 A1 * | 12/2021 | Scheinberg | A43B 7/28 |

* cited by examiner

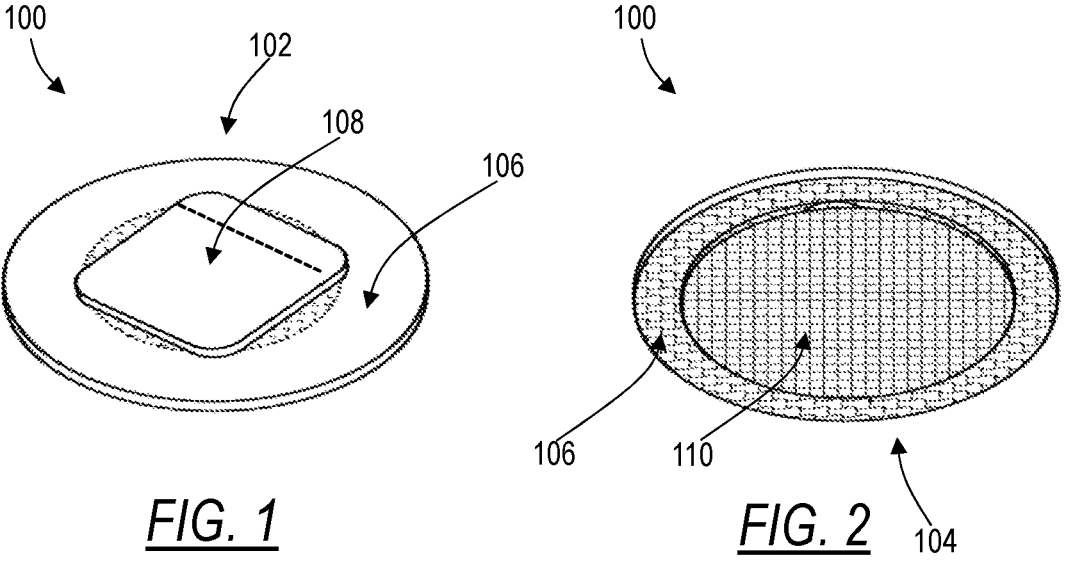
*FIG. 1*          *FIG. 2*
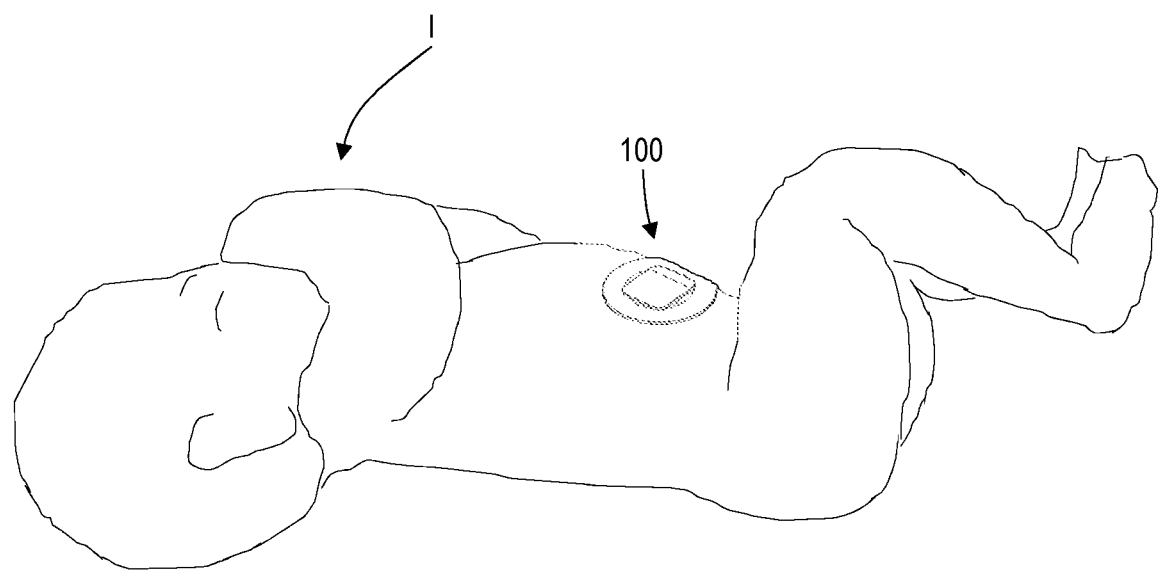
*FIG. 3*

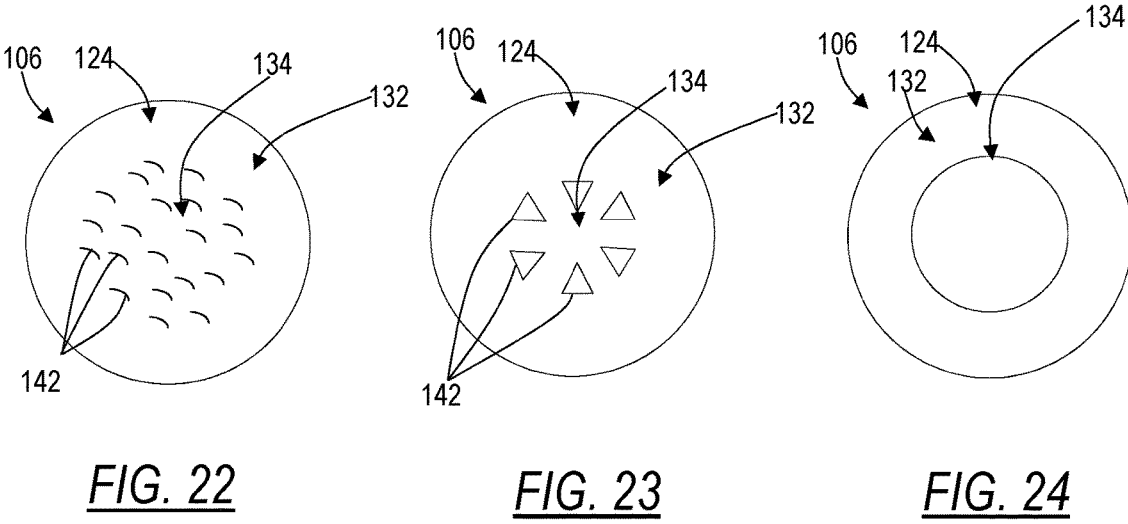
*FIG. 22*        *FIG. 23*        *FIG. 24*
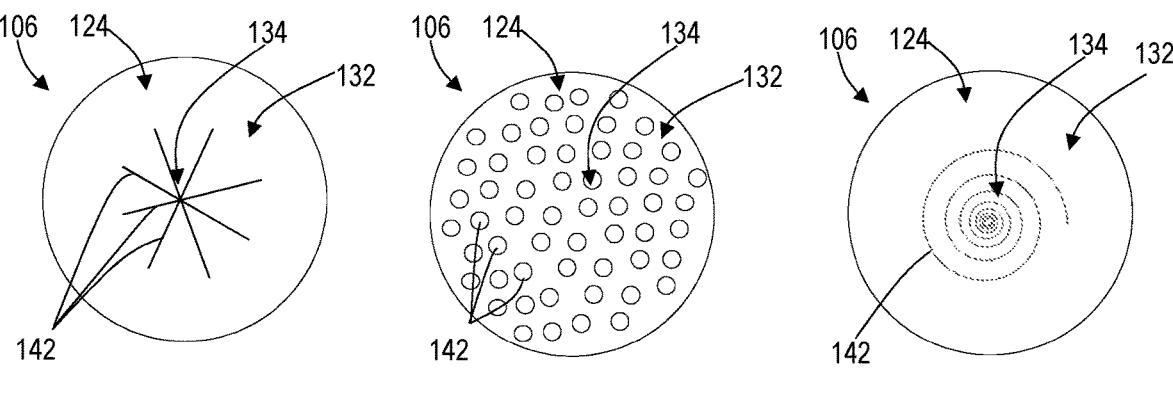
*FIG. 25*        *FIG. 26*        *FIG. 27*

UMBILICAL CORD STUMP PROTECTOR

FIELD

This relates to the field of infant care and, more particularly, to protecting an infant's umbilical cord stump.

BACKGROUND

After birth, an infant's umbilical cord is usually clamped in two sections, between which the medical professional will sever the cord. After the umbilical cord is severed, the cord is clamped closer to the infant's naval and cut to reach its final length between three to five centimeters. After the umbilical cord stump dries, the clamp may be removed. Healing may take two to three weeks, during which time the cord stump falls off on its own.

The cord stump is suspected to be an inlet for bacteria colonization in an infant's bloodstream. The current recommended medical course of action is to leave the cord stump exposed to air while avoiding contamination or irritation. If the cord stump does become contaminated with urine or another substance, pediatricians usually recommend cleaning it with mild soap and water using a cotton ball, then patting it dry. At times, pediatricians may suggest using antimicrobial agents, however, many substances are known to hinder the healing process by damaging healthy skin cells.

Due to the importance of cord stump hygiene, parents often become fearful. The cord stump can tear if an external source creates irritation, which can increase the likelihood of infection. New parents usually take extreme caution and care in avoiding the umbilicus area during the first 10-14 days after birth until the cord stump dries and detaches from the infant's naval.

Umbilical stump care options on the market include waterproof adhesive pad covers used on wounds and hernia belts. The waterproof adhesive pad covers are meant to allow the infant to swim with the parents or to be given a bath. The hernia belts are to be used to help protect against external tearing or irritation. Additionally, certain clothing and diapers sometimes include a feature designed prevent the umbilical cord area from being irritated.

BRIEF SUMMARY

The drawback of these options is that they either press against the cord stump, which can cause irritation, or they do not provide a relatively easy mechanism for protecting the cord stump while also permitting it to be cleaned. This disclosure describes examples of a umbilical cord stump protector that overcomes these drawbacks.

A first example of the infant umbilical cord stump protector includes a pad positionable proximal to an umbilical cord stump and a cover including fluid impermeable material over the pad. The fluid impermeable material has (i) an adhesive region that is adhereable to an infant about the umbilical cord stump, (ii) a deformable region, and (iii) a periphery about the deformable region. The deformable region has greater flexibility than the periphery in such a way that the cover forms a dome-like shape about the umbilical cord stump.

The following additional features may be included in the first example of the umbilical cord stump protector.

A seal including fluid impermeable material may be adhered to the cover over the deformable region.

The deformable region may define a cut through the fluid impermeable material of the cover.

The deformable region may define a cut through the fluid impermeable material of the cover and a seal including fluid impermeable material may be adhered to the cover over the cut.

The pad may be adhered to the cover.

The pad may be adhered to the cover, which causes the pad to emulate the dome-like shape of the cover about the umbilical cord stump.

The deformable region may defines a cut through the fluid impermeable material of the cover while a seal including fluid impermeable material is adhered to the cover over the cut and the pad is adhered to the cover under the cut.

A water vapor transmission rate (WVTR) of the fluid impermeable material of the cover may be greater than 0 $g/m^2$ per 24 hours and up to 10,000 $g/m^2$ per 24 hours.

A second example of the infant umbilical cord stump protector includes a pad adhered to skin of an infant proximal to an umbilical cord stump and a cover including fluid impermeable material. The fluid impermeable material has (i) an adhesive adhered to the skin and pad, (ii) a deformable region, and (iii) a periphery about the deformable region. The deformable region has greater flexibility than the periphery in such a way that the cover forms a dome-like shape about the umbilical cord stump and pad. A seal including fluid impermeable material is adhered to the cover over the deformable region.

The following additional features may be included in the second example of the umbilical cord stump protector.

The deformable region may define a cut through the fluid impermeable material of the cover.

The deformable region may define a cut through the fluid impermeable material of the cover and the seal may be adhered to the cover over the cut.

The pad may be adhered to the cover which causes the pad to emulate the dome-like shape of the cover about the umbilical cord stump.

The deformable region may define a cut through the fluid impermeable material of the cover while a seal including fluid impermeable material is adhered to the cover over the cut and the fluid absorbent material is adhered to the cover under the cut.

A water vapor transmission rate (WVTR) of the fluid impermeable material of the cover may be greater than 0 $g/m^2$ per 24 hours and up to 10,000 $g/m^2$ per 24 hours.

A third example of the infant umbilical cord stump protector includes a pad positionable proximal to an umbilical cord stump and a cover including fluid impermeable material over the pad. The fluid impermeable material has (i) an adhesive region that is adhereable to an infant about the umbilical cord stump and (ii) a central region defining an opening in the fluid impermeable material. A seal including fluid impermeable material is adhered to the cover and covering over the opening.

The following additional features may be included in the third example of the umbilical cord stump protector.

The pad may be adhered to the cover under the opening.

The cover may include a deformable region defining the opening and a periphery about the deformable region where the deformable region has greater flexibility than the periphery in such a way that the cover forms a dome-like shape about the umbilical cord stump and pad and the pad is adhered to the cover, which causes the pad to emulate the dome-like shape of the cover about the umbilical cord stump.

The pad may extend upwardly through the opening and contact the seal.

A water vapor transmission rate (WVTR) of the fluid impermeable material of the cover may be greater than 0 g/m² per 24 hours and up to 10,000 g/m² per 24 hours.

An example of a method of protecting an infant umbilical cord stump includes positioning a pad proximal to an umbilical cord stump and forming a dome-like shape in a cover including fluid impermeable material over the pad. The fluid impermeable material has (i) an adhesive region, (ii) a deformable region, and (iii) a periphery about the deformable region. The deformable region has greater flexibility than the periphery. The adhesive region is adhered to an infant's skin about the umbilical cord stump.

The following additional features may be included in the method.

A seal including fluid impermeable material may be adhered to the cover over the deformable region.

The deformable region may define a cut through the fluid impermeable material of the cover.

The deformable region may define a cut through the fluid impermeable material of the cover and a seal including fluid impermeable material may be adhered to the cover over the cut.

The pad may be adhered to the cover.

The pad may be adhered to the cover, which causes the pad to emulate the dome-like shape of the cover about the umbilical cord stump.

The deformable region may define a cut through the fluid impermeable material of the cover while a seal including fluid impermeable material is adhered to the cover over the cut and the pad is adhered to the cover under the cut.

A water vapor transmission rate (WVTR) of the fluid impermeable material of the cover may be greater than 0 g/m² per 24 hours and up to 10,000 g/m² per 24 hours.

BRIEF DESCRIPTION OF THE DRAWINGS

FIG. 1 is a top side perspective view of an example of an umbilical cord stump protector.

FIG. 2 is a bottom side perspective view thereof.

FIG. 3 is a depiction of an infant wearing the umbilical cord stump protector of FIGS. 1 and 2.

4

Figures 16, 17, 18:
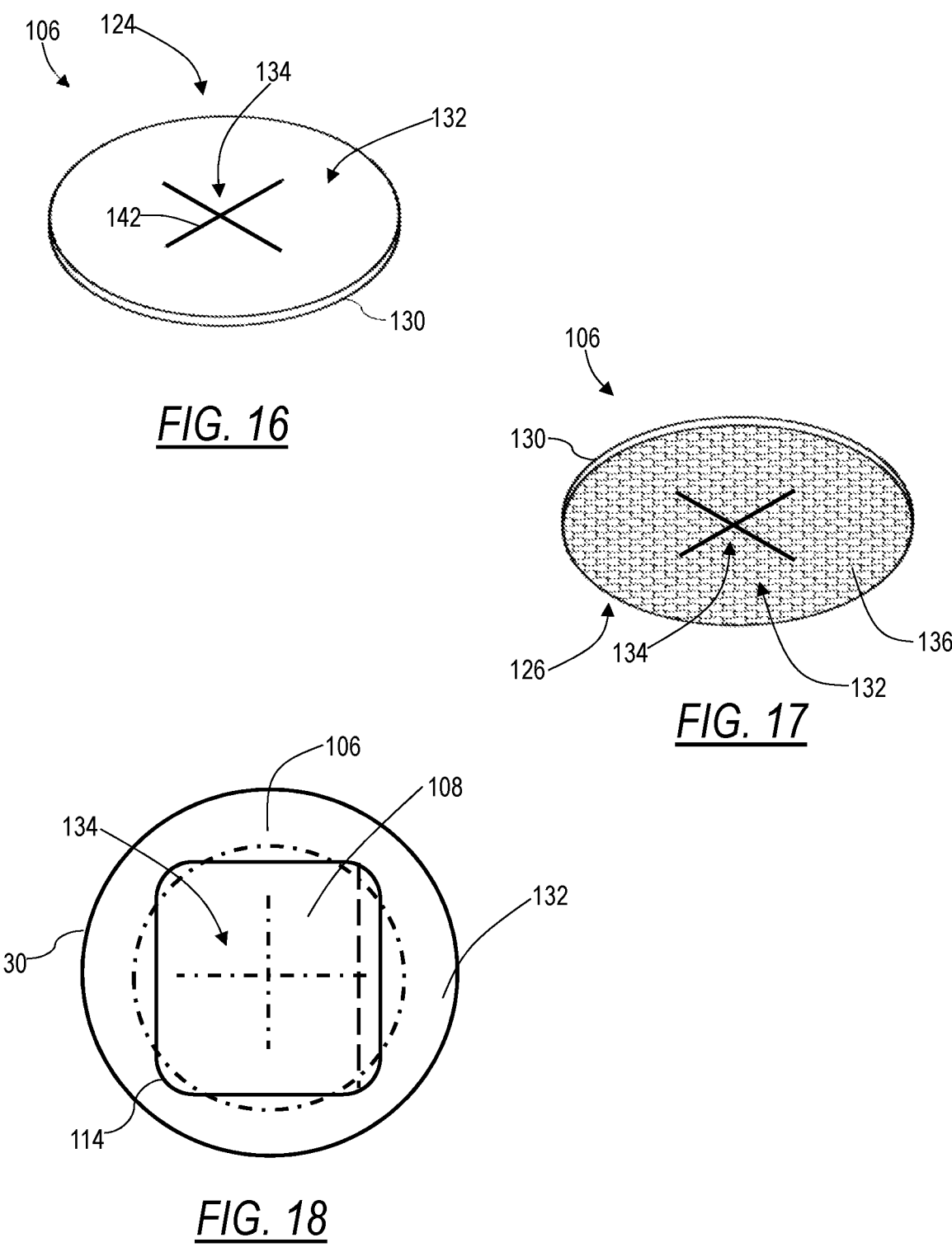
FIG. 16 is a top side perspective view of a different example of the cover.
FIG. 17 is a bottom side perspective view thereof.
FIG. 18 is a top view of a different example of the umbilical cord stump protector including the cover of FIGS. 16 and 17.
Figure 19:
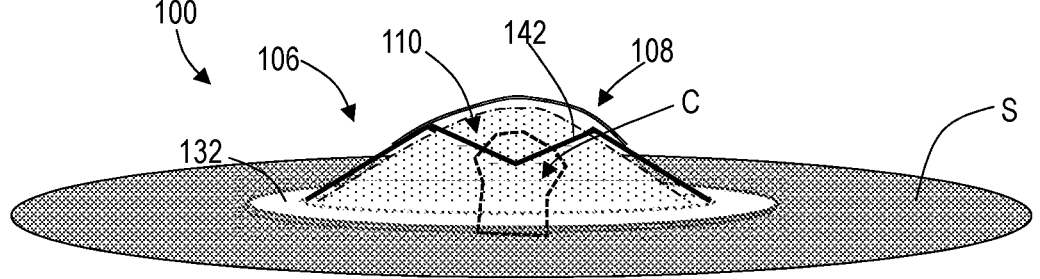

FIG. 19 is a side close up view of the umbilical cord stump protector of FIG. 18 positioned on an infant over the umbilical cord stump.

Figure 20:
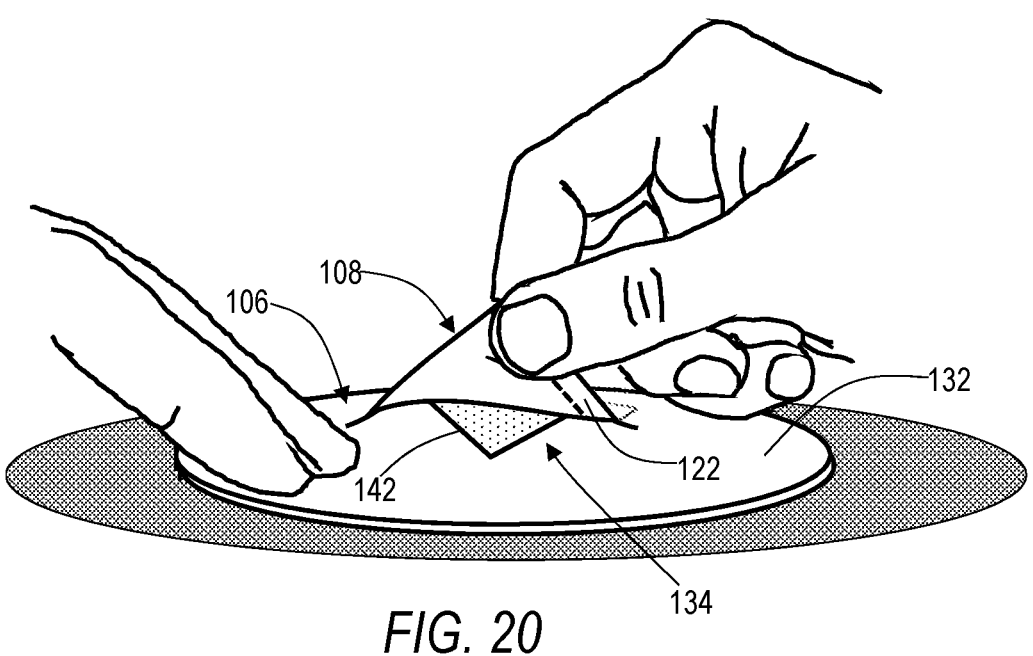

FIG. 20 is a side close up view of the umbilical cord stump protector of FIG. 18 positioned on an infant over the umbilical cord stump while the seal is being removed.

Figure 21:
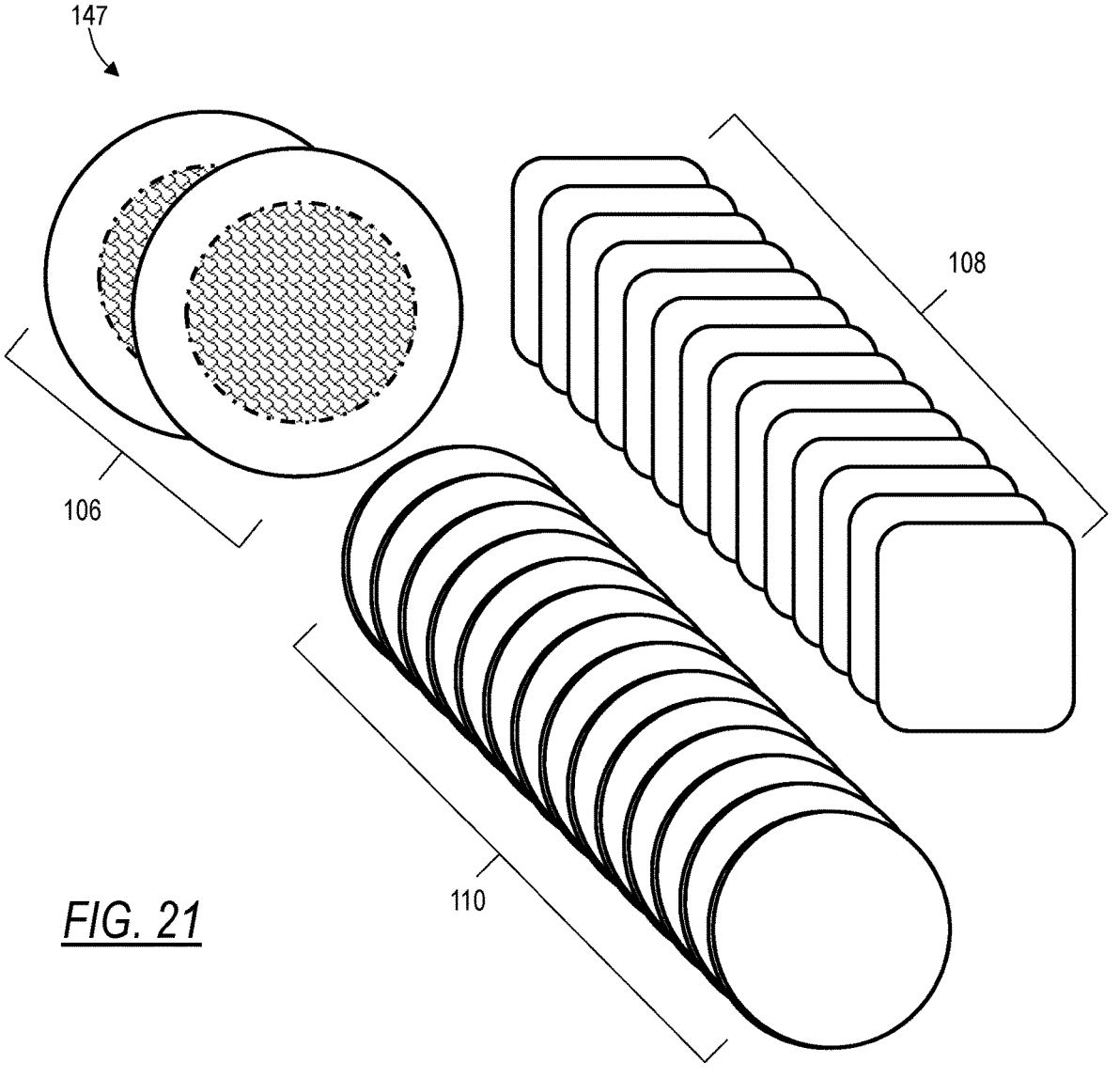

FIG. 21 is illustrates a kit containing multiple covers, seals, and pads.

FIG. 22 is a top view of a third example of the cover.

FIG. 23 is a top view of a fourth example of the cover.

FIG. 24 is a top view of a fifth example of the cover.

FIG. 25 is a top view of a sixth example of the cover.

FIG. 26 is a top view of a seventh example of the cover.

FIG. 27 is a top view of an eighth example of the cover.

Figure 28:
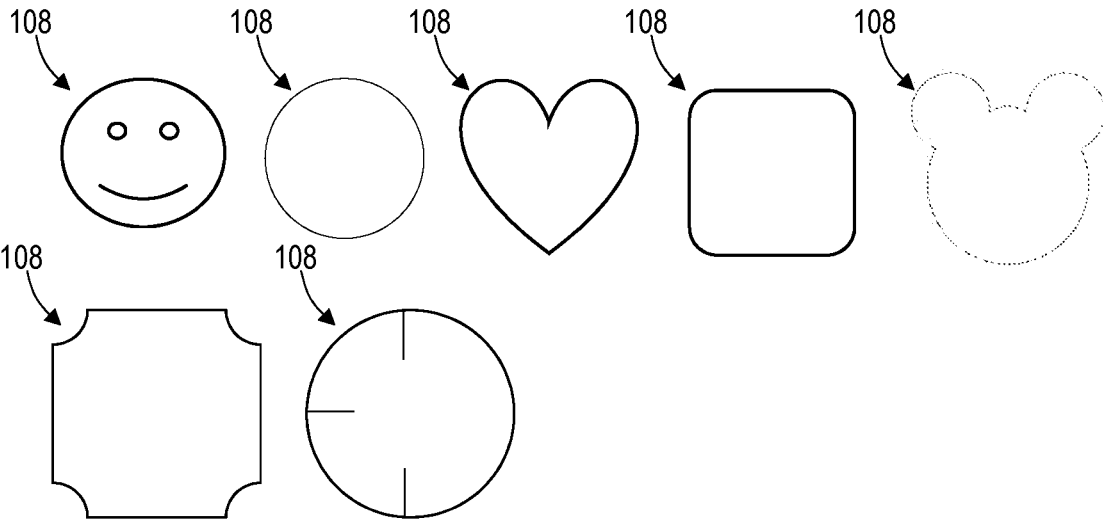

FIG. 28 is a top view of different possible examples of the seal.

DETAILED DESCRIPTION OF EXAMPLES

This disclosure describes examples and aspects, but not all possible examples or aspects of the umbilical cord stump protector and related methods. Where a particular feature is disclosed in the context of a particular aspect or example, that feature can also be used, to the extent possible, in combination with and/or in the context of other aspects and examples. The umbilical cord stump protector may be embodied in many different forms and should not be construed as limited to only the examples described here.

Referring to FIGS. 1-3, an example of the umbilical cord stump protector 100 includes a top side 102, bottom side 104, cover 106, seal 108, and a pad 110. The stump protector 100 is designed to be positioned over and cover an umbilical cord stump of an infant I, while the stump is attached to the infant's umbilicus. The stump protector 100 advantageously protects the cord stump on newborn infants as it dries and eventually falls off. It provides a fluid absorbent interior that absorbs fluid from the cord stump and umbilicus while also providing a substantially fluid proof barrier over the cord stump to prevent infection and irritation.

Figure 4:
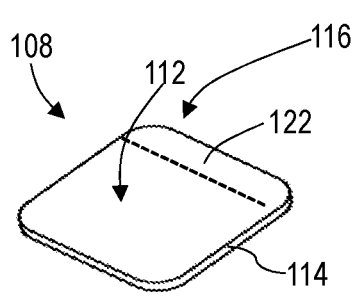
FIG. 4 is a top side perspective view of an example of the seal.
Figure 5:
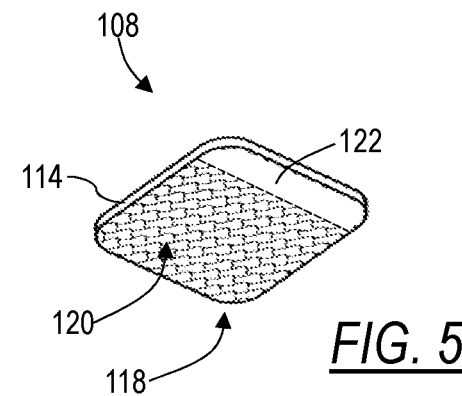
FIG. 5 is a bottom side perspective view thereof.

Referring to FIGS. 4 and 5, an example of the seal 108 includes a substantially fluid impermeable seal body 112 defining a seal perimeter 114 and having a seal top side 116 and a seal bottom side 118. The seal 108 includes an adhesive seal surface 120 that at least partially covers the seal bottom side 118.

An optional tab 122, configured to be pulled for removal of the seal 108 from the cover 106, is positioned along an edge of the seal 108. The adhesive seal surface 120 in this example does not extend onto the tab 122 on the seal bottom side 118, but it can in other examples. The tab 122 leaves the edge of the seal 108 free and non-adhered to the cover 106 so that a user can easily grab the tab 122 with their fingers and pull it off the cover 106 when desired by de-adhering the seal 108 from the cover 106.

Figure 6:
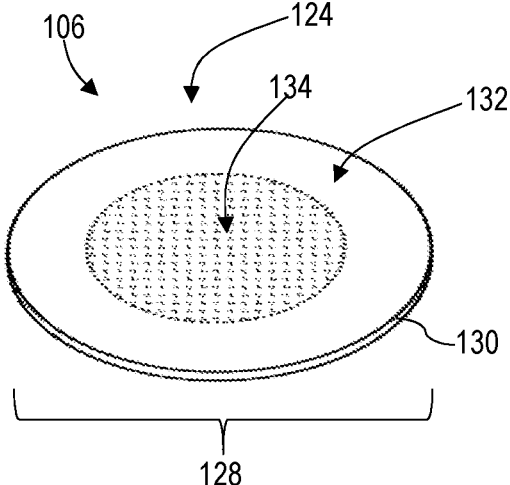
FIG. 6 is a top side perspective view of an example of the cover.
Figure 7:
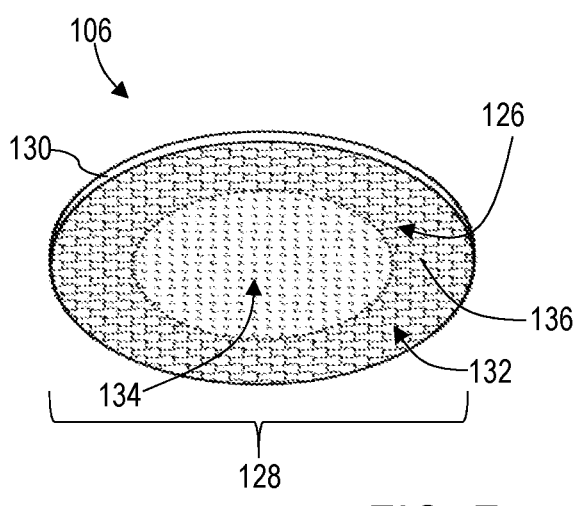
FIG. 7 is a bottom side perspective view thereof.

Referring to FIGS. 6 and 7, an example of the cover 106 includes a cover top side 124, a cover bottom side 126, and a substantially fluid impermeable cover body 128 defining a cover perimeter 130. The cover body 128 includes a periphery 132 surrounding a deformable region 134 at the central portion of the cover 106. The deformable region 134 has more flexibility than the periphery 132, which makes the deformable region 134 more easily formable into a dome-like shape over the cord stump while the periphery 132 serves as a less flexible structural support around the deformable region 134. The periphery 132 and deformable region 134 may be including the same substantially fluid impermeable material.

There are many ways to give the deformable region 134 more flexibility than the periphery 132. These may include, for example, making the substantially fluid impermeable material thinner at the deformable region 134 than the periphery 132, including perforations in the substantially fluid impermeable material at the deformable region 134, and/or forming one or more cuts through the substantially fluid impermeable material of the deformable region 134. A few possible examples of the cover 106 with differently constructed deformable regions 134 will be described later.

The cover bottom side 126 includes an adhesive cover surface 136 that at least partially covers the cover bottom side 126. The adhesive cover surface 136 may extend over only the periphery 132 or the periphery 132 and the deformable region 134.

The fluid impermeable material used for the cover 106 and seal 108 may be the same material or a different material. The fluid impermeable material may be including a thin sheet of a plastic or plastic-like material such as, for example, polyurethane, polyethylene, rubber, silicone, vinyl, polyvinylchloride, or the like. Other possible fluid impermeable materials include treated fabrics, bamboo, and foam.

The fluid impermeable material may be completely occlusive to moisture or it may be breathable to permit moisture vapor to pass through it, which may help the cord stump dry. In an example in which the fluid impermeable material is breathable, the water vapor transmission rate (WVTR) of the fluid impermeable material may be greater than 0 g/m$^2$ per 24 hours to 10,000 g/m$^2$ per 24 hours.

The adhesive cover surface 136 is designed to adhere the cover perimeter 130 to the infant's skin and form a substantially fluid tight seal against the skin. Because it contacts the infant's skin, a low trauma adhesive may be used. Examples of low trauma adhesives include, for example, low trauma water insoluble adhesive such as a silicone adhesive or the like.

Figure 8:
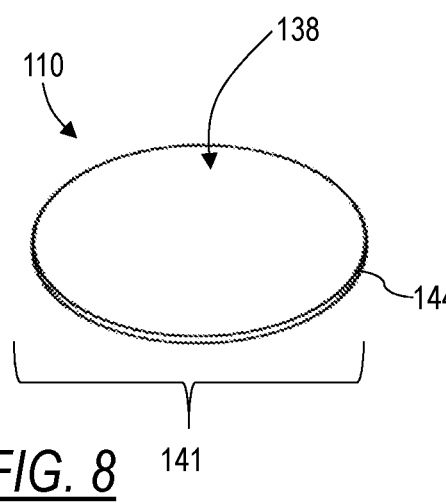
FIG. 8 is a top side perspective view of an example of the pad.
Figure 9:
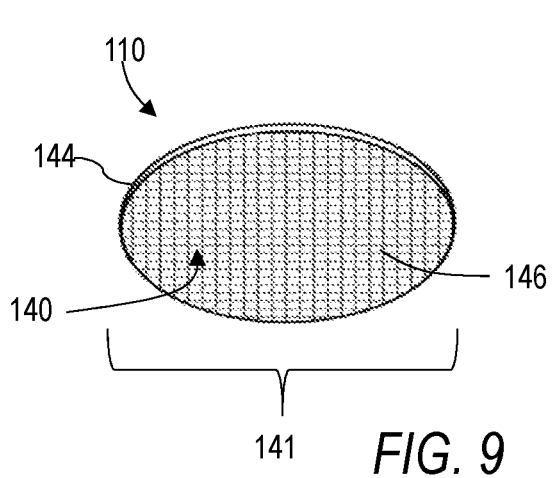
FIG. 9 is a bottom side perspective view thereof.

Referring to FIGS. 8 and 9, an example of the pad 110 includes a pad top side 138, a pad bottom side 140, and a pad body 141 defining a pad perimeter 144. The pad body 141 may be primarily including a fluid absorbent material such as polyester, lyocell, wool, cotton, nylon, hydrocolloid, hydrogel, bamboo, microfiber, lycra, polyurethane, foam, or the like.

The pad bottom side 140 is optionally covered by a substantially non-stick material 146 that minimizes sticking between the fluid absorbent material, the cord stump, and the infant's skin. This helps prevent the pad 110 from irritating the infant's skin or the cord stump or sticking to the cord stump. This also help minimize sticking between the cord stump and fluid absorbent material due to exudate produced by the cord stump, which when left behind can lead to colonization of bacteria. Such a non-stick material may be a non-stick material used to cover conventional adhesive bandage pads. Examples of such non-stick materials may include, for example, a perforated polyethylene film, or the like.

The pad 110 provides cushioning for extra protection from knocking the cord stump and provides moisture wicking to remove excess exudate and help dry the stump. The drying process may also be assisted by giving the pad 110 a high water vapor transmission rate, which allows moisture to be released into the air. The pad 110 is flexible and may optionally include slits or cuts to improve the conformity to the umbilical cord stump if desired.

The construction of the stump protector 100 will now be discussed by referring to FIGS. 10-13. The seal 108, cover

106, and pad 110 may be combined into a single composite structure in which the seal 108 is adhered to the cover top side 124 using the adhesive seal surface 120 and the pad top side 138 is adhered to the cover bottom side 126 using the adhesive cover surface 136.

Figures 10, 11, 12, 13:
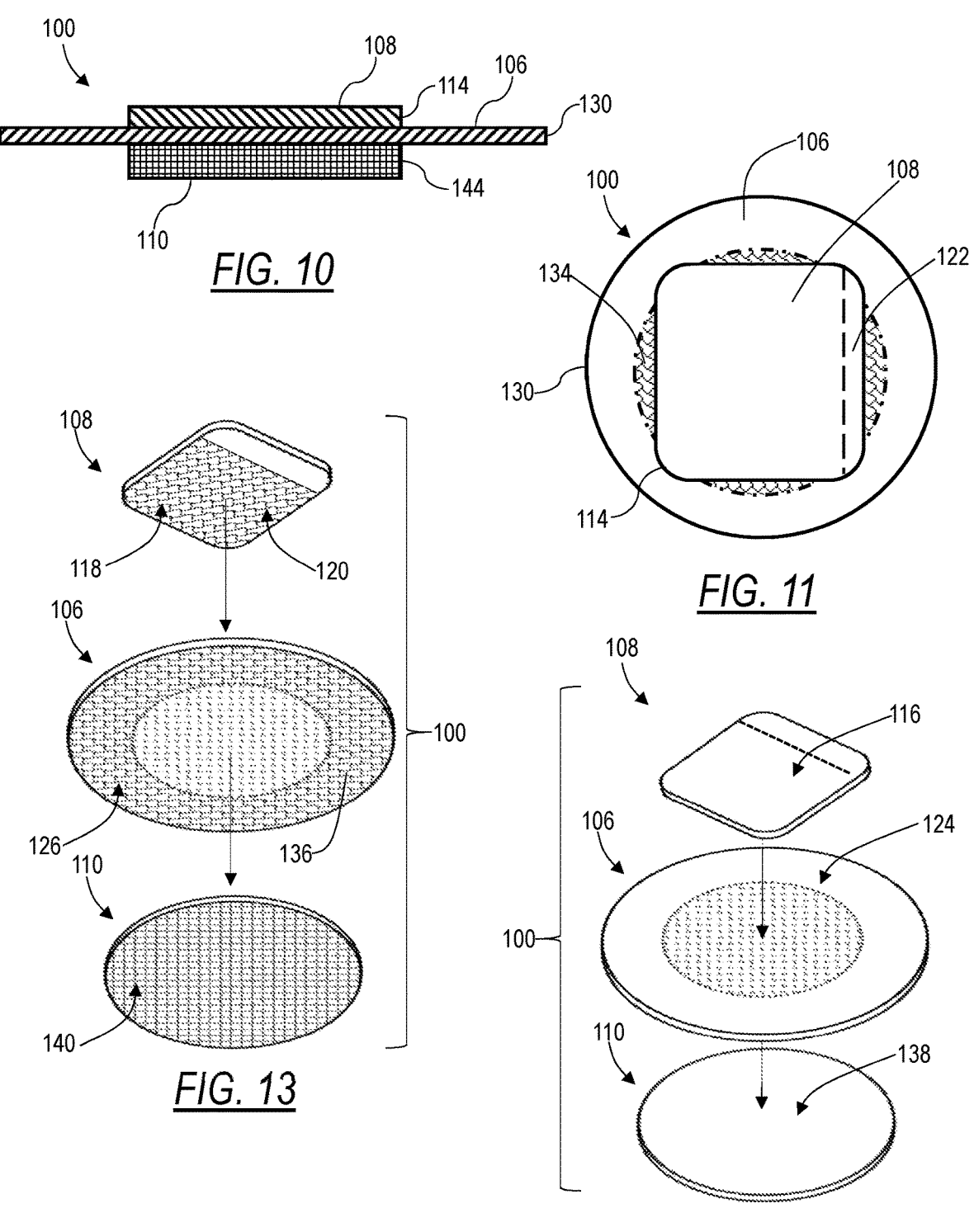
FIG. 10 is a side view of the umbilical cord stump protector of FIGS. 1 and 2.
FIG. 11 is a top view thereof.
FIG. 12 is an exploded top perspective view thereof.
FIG. 13 is an exploded bottom perspective view thereof.

As indicated by the arrows in FIGS. 12 and 13, the seal 108, cover 106, and pad 110 are aligned along a common axis such that the axis passes through the center of each of these components.

The cover perimeter 130 extends outwardly beyond the seal perimeter 114 and pad perimeter 144. This permits the cover 106 to substantially enclose the pad 110 and form a substantially fluid tight seal around the pad 110 when the stump protector is being worm by the infant.

Figure 14:
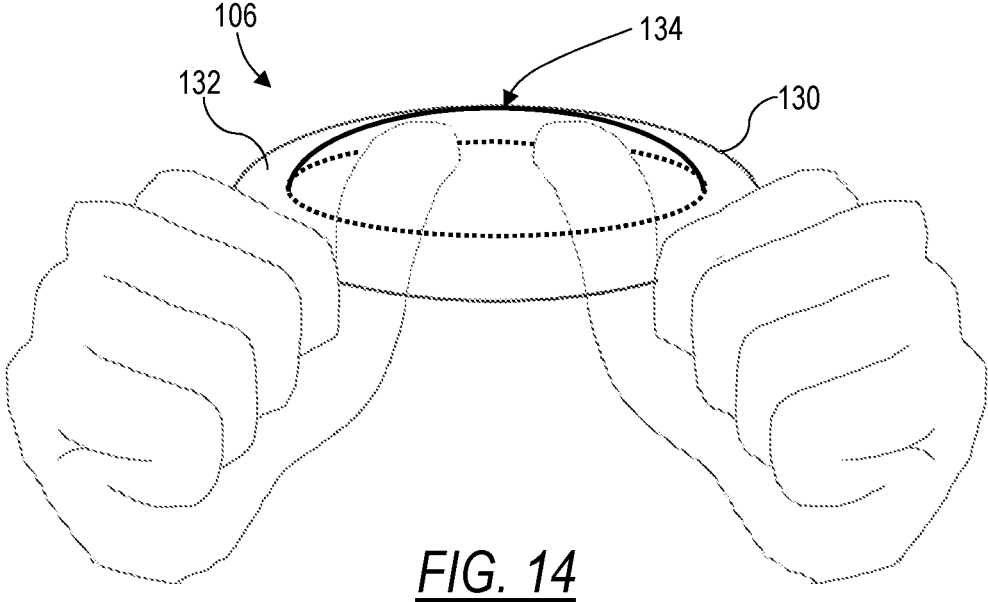
FIG. 14 illustrates using a person's fingers to deform the deformable region of the cover.

Referring to FIG. 14, the cover 106 is shown alone to illustrate an advantageous feature of the stump protector 100, namely, that the cover 106 can be deformed from a substantially flat shape into a dome-like shape by pressing against the deformable region 134 while holding the periphery 132. In use, the pad 110 may be attached to the cover 106 while this deformation is taking place so that the pad 110 will assume or mimic the dome-like shape of the deformed cover 106. The adherence of the adhesive cover surface 136 to the pad 110 may force the pad 110 to emulate the dome-like shape of the deformed cover 106.

Figure 15:
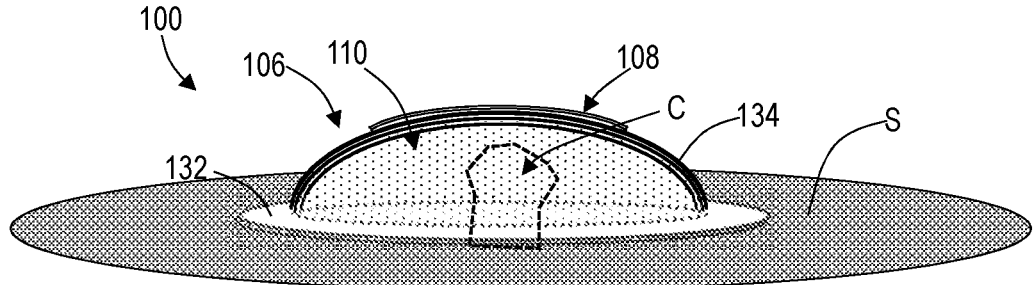
FIG. 15 is a side close up view of the umbilical cord stump protector of FIGS. 1 and 2 positioned on an infant about the umbilical cord stump.

Referring to FIG. 15, after the dome-like shape is formed, and the stump protector 100 is placed on the infant, the cord stump C is protected within the dome-like shape while the periphery 132 is adhered to the infant's skin S. The dome-like shape is designed to mitigate the degree to which the stump protector 100 presses against the cord stump C and thus mitigates the risk of irritation. At the same time, the stump protector 100, provides a fluid barrier to the cord stump C to mitigate the risk of irritation and infection due to unwanted fluids contacting the cord stump C.

Referring to FIGS. 16-20, a different example of the cover 106 is shown using the same reference numerals to refer to the same features of both examples. In this example, the deformable region 134, includes at least one cut 142 that extends through the cover 106 from the cover top side 124 to the cover bottom side 126. The cut 142 may be a single straight cut or be a cross-like shape as shown.

Referring to FIG. 18, the stump protector 100, including the cover 106 of FIGS. 16 and 17, is shown. The seal 108 extends completely over the cut 142 such that the cut 142 is completely within the seal perimeter 114. When the deformable region 134 of this example of the cover 106 is deformed as in FIG. 14, the cut 142 defines an opening through the cover 106 and the seal 108 seals the opening.

The portion of the seal 108 that contacts the pad 110 may be substantially free of adhesive if desired.

In FIG. 19, the stump protector 100 with the cover of FIGS. 16-17 is being worn by the infant. In this case, the cover 106 and pad 110 have been formed into the dome-like shape, placed around the cord stump C, and the periphery 132 has been adhered to the infant's skin S. Upon deformation, the cut 142 forms an opening through which a portion of the pad 110 extends and comes into contacts with the seal 108. The seal 108 remains adhered to the cover 106, which provides a substantially fluid tight seal over the pad 110.

Referring to FIG. 20, the seal 108 may be removed, if desired, such as to access a pad 110 that has been soiled or otherwise needs to be replaced. The user may easily remove the seal 108 by pulling the tab 122 outwardly such that the adhesive seal surface 120 de-adheres from the cover 106.

Referring to FIG. 21, the stump protector 100 may be provided in a kit 147 containing a plurality of covers 106, seals 108, and pads 110. Such a kit 147 will allow the user to replace pads 110 that are dirty and seals 108 that may have become dirty or have lost their ability to provide a substantially fluid tight seal for some reason.

Additional examples of covers 106 are shown in FIGS. 22-27 using the same reference numerals to refer to the same features as in the previous two examples.

In the cover 106 of FIG. 22, the deformable region 134 includes a plurality of cuts 142 individually formed around the center of the cover 106. These individual cuts 142 impart more flexibility to the deformable region 134 than the periphery.

In the cover 106 of FIG. 23, the deformable region 134 includes a plurality of cuts 142 that are triangular and arranged concentrically about the center of the cover 106. This arrangement imparts more flexibility to the deformable region 134 than the periphery 132.

In the cover 106 of FIG. 24, the deformable region defines an opening through the fluid impermeable material.

The cover 106 of FIG. 25 functions in a similar manner as the cover 106 in FIGS. 16-20, but the cut 142 includes an additional cross-shaped cut that is angularly offset relative to the cross-shaped cut in the cover 106 of FIGS. 16-20, which may impart added flexibility to the deformable region 134.

In the cover 106 of FIG. 26, the deformable region 134 includes a plurality of cuts 142 defining circular holes through the cover 106. These circular holes impart more flexibility to the deformable region 134 than the periphery 132.

In the cover 106 of FIG. 27, the deformable region 134 includes a cut 142 that spirals inward toward the center of the cover 106. Such a spiral shaped cut 142 imparts more flexibility to the deformable region 134 than the periphery 132.

Referring to FIG. 28, different possible examples of the seal 108 are shown. The seal 108 may have many different shapes and sizes depending on what is desired.

The umbilical cord stump protector 100 may be modified in many different ways without departing from the scope of what is claimed. The scope of the claims is not limited to the particular features and examples described above.

That which is claimed is:

1. An apparatus comprising an infant umbilical cord stump protector including:
 a pad positionable proximal to an umbilical cord stump; and
 a cover including fluid impermeable material over the pad, the fluid impermeable material having (i) an adhesive region that is adhereable to an infant about the umbilical cord stump, (ii) a deformable region defining a cut through the fluid impermeable material of the cover, and (iii) a periphery about the deformable region, the deformable region having greater flexibility than the periphery in such a way that the cover is configured to form a dome-like shape about the umbilical cord stump.

2. The apparatus of claim 1, further comprising a seal including fluid impermeable material adhered to the cover over the deformable region.

3. The apparatus of claim 1, wherein a seal including fluid impermeable material is adhered to the cover over the cut.

4. The apparatus of claim 1, wherein the pad is adhered to the cover.

5. The apparatus of claim 1, wherein the pad is adhered to the cover which causes the pad to emulate the dome-like shape of the cover to be configured about the umbilical cord stump.

6. The apparatus of claim 1, wherein:
 a seal including fluid impermeable material is adhered to the cover over the cut; and
 the pad is adhered to the cover under the cut.

7. The apparatus of claim 1, wherein a water vapor transmission rate (WVTR) of the fluid impermeable material of the cover is greater than 0 g/m$^2$ per 24 hours and up to 10,000 g/m$^2$ per 24 hours.

8. The apparatus of claim 2, wherein the seal is removable from the deformable region by pulling a tab on the seal.

9. The apparatus of claim 1, wherein the pad is removeable and replaceable.

10. An apparatus comprising an infant umbilical cord stump protector including:
 a pad configured to be adhered to skin of an infant proximal to an umbilical cord stump;
 a cover including fluid impermeable material, the fluid impermeable material having (i) an adhesive configured to be adhered to the skin and pad, (ii) a deformable region defining a cut through the fluid impermeable material of the cover, and (iii) a periphery about the deformable region, the deformable region having greater flexibility than the periphery in such a way that the cover is configured to form a dome-like shape about the umbilical cord stump and pad; and
 a seal including fluid impermeable material adhered to the cover over the deformable region.

11. The apparatus of claim 10, wherein the seal is adhered to the cover over the cut.

12. The apparatus of claim 10, wherein the pad is adhered to the cover which causes the pad to emulate the dome-like shape of the cover about the umbilical cord stump.

13. The apparatus of claim 10, wherein:
 the seal including fluid impermeable material is adhered to the cover over the cut; and
 the pad is adhered to the cover under the cut.

14. The apparatus of claim 10, wherein a water vapor transmission rate (WVTR) of the fluid impermeable material of the cover is greater than 0 g/m$^2$ per 24 hours and up to 10,000 g/m$^2$ per 24 hours.

15. The apparatus of claim 10, wherein the seal is removable from the deformable region by pulling a tab on the seal.

16. The apparatus of claim 10, wherein the pad is removeable and replaceable.

17. A method comprising protecting an infant umbilical cord stump by:
 positioning a pad proximal to an umbilical cord stump; and
 forming a dome-like shape in a cover including fluid impermeable material over the pad, the fluid impermeable material having (i) an adhesive region, (ii) a deformable region defining a cut through the fluid impermeable material of the cover, and (iii) a periphery about the deformable region, the deformable region having greater flexibility than the periphery; and
 adhering the adhesive region to an infant's skin about the umbilical cord stump.

18. The method of claim 17, further comprising a seal including fluid impermeable material adhered to the cover over the deformable region.

19. The method of claim 17, wherein a seal including fluid impermeable material is adhered to the cover over the cut.

20. The method of claim 17, wherein the pad is adhered to the cover.

21. The method of claim 17, wherein the pad is adhered to the cover which causes the pad to emulate the dome-like shape of the cover about the umbilical cord stump.

22. The method of claim 17, wherein:

a seal including fluid impermeable material is adhered to the cover over the cut; and the pad is adhered to the cover under the cut.

23. The method of claim 17, wherein a water vapor transmission rate (WVTR) of the fluid impermeable material of the cover is greater than 0 g/m² per 24 hours and up to 10,000 g/m² per 24 hours.

24. The method of claim 19, wherein the seal is removable from the deformable region by pulling a tab on the seal.

25. The method of claim 17, wherein the pad is removeable and replaceable.

26. An apparatus comprising an infant umbilical cord stump protector including:

a pad positionable proximal to an umbilical cord stump; and a cover including fluid impermeable material over the pad, the fluid impermeable material having (i) an adhesive region that is adhereable to an infant about the umbilical cord stump and (ii) a central region defining an opening in the fluid impermeable material; and a seal including fluid impermeable material adhered to the cover and covering the opening.

27. The apparatus of claim 26, wherein the pad is adhered to the cover under the opening.

28. The apparatus of claim 26, wherein:

the cover includes a deformable region defining the opening and a periphery about the deformable region, the deformable region having greater flexibility than the periphery in such a way that the cover is configured to form a dome-like shape about the umbilical cord stump and pad; and the pad is adhered to the cover which causes the pad to emulate the dome-like shape of the cover to be configured about the umbilical cord stump.

29. The apparatus of claim 26, wherein the pad extends upwardly through the opening and contacts the seal.

30. The apparatus of claim 26, wherein a water vapor transmission rate (WVTR) of the fluid impermeable material of the cover is greater than 0 g/m² per 24 hours and up to 10,000 g/m² per 24 hours.

31. The apparatus of claim 28, wherein the seal is adhered to the cover over the deformable region and the seal is removable from the deformable region by pulling a tab on the seal.

32. A method comprising protecting an infant umbilical cord stump by:

positioning a pad proximal to an umbilical cord stump; and forming a dome-like shape in a cover including fluid impermeable material over the pad, the fluid impermeable material having (i) an adhesive region, (ii) a deformable region, and (iii) a periphery about the deformable region, the deformable region having greater flexibility than the periphery;

adhering the adhesive region to an infant's skin about the umbilical cord stump;

wherein forming the dome-like shape includes deforming the cover from flat to concave; and further comprising covering the umbilical cord stump with the cover concave until the umbilical cord stump dries.

33. The method of claim 32, wherein the cover includes a seal including fluid impermeable material adhered to the cover over the deformable region.

34. The method of claim 32, wherein the deformable region defines a cut through the fluid impermeable material of the cover.

35. The method of claim 32, wherein the deformable region defines a cut through the fluid impermeable material of the cover and a seal including fluid impermeable material is adhered to the cover over the cut.

36. The method of claim 32, wherein the pad is adhered to the cover which causes the pad to emulate the dome-like shape of the cover to be configured about the umbilical cord stump.

37. The method of claim 32, wherein:

the deformable region defines a cut through the fluid impermeable material of the cover;

a seal including fluid impermeable material is adhered to the cover over the cut; and the pad is adhered to the cover under the cut.

38. The method of claim 32, wherein the pad is removeable and replaceable.

39. The method of claim 33, further comprising removing the seal from the deformable region by pulling a tab on the seal.

40. An apparatus comprising an infant umbilical cord stump protector including:

a pad positionable proximal to an umbilical cord stump; and a cover including fluid impermeable material over the pad, the fluid impermeable material having (i) an adhesive region that is adhereable to an infant about the umbilical cord stump, (ii) a deformable region, and (iii) a periphery about the deformable region, the deformable region having greater flexibility than the periphery in such a way that the cover is configured to form a dome-like shape about the umbilical cord stump; and a seal including fluid impermeable material adhered to the cover over the deformable region, the seal being removable from the deformable region by pulling a tab on the seal.

41. The apparatus of claim 40, wherein the deformable region defines a cut through the fluid impermeable material of the cover.

42. The apparatus of claim 40, wherein the deformable region defines a cut through the fluid impermeable material of the cover and the seal including fluid impermeable material is adhered to the cover over the cut.

43. The apparatus of claim 40, wherein the pad is adhered to the cover which causes the pad to emulate the dome-like shape of the cover to be configured about the umbilical cord stump.

44. The apparatus of claim 40, wherein:

the deformable region defines a cut through the fluid impermeable material of the cover;

the seal including fluid impermeable material is adhered to the cover over the cut; and the pad is adhered to the cover under the cut.

45. The apparatus of claim 40, wherein the pad is removeable and replaceable.

46. An apparatus comprising an infant umbilical cord stump protector including:

a pad positionable proximal to an umbilical cord stump; and a cover including fluid impermeable material over the pad, the fluid impermeable material having (i) an adhesive region that is adhereable to an infant about the umbilical cord stump, (ii) a deformable region, and (iii) a periphery about the deformable region, the deformable region having greater flexibility than the periphery in such a way that the cover is configured to form a dome-like shape about the umbilical cord stump; and a seal including fluid impermeable material adhered to the cover over the deformable region, the seal being removable from the deformable region.

47. The apparatus of claim 46, wherein the deformable region defines a cut through the fluid impermeable material of the cover.

48. The apparatus of claim 46, wherein the deformable region defines a cut through the fluid impermeable material of the cover and the seal including fluid impermeable material is adhered to the cover over the cut.

49. The apparatus of claim 46, wherein the pad is adhered to the cover which causes the pad to emulate the dome-like shape of the cover to be configured about the umbilical cord stump.

50. The apparatus of claim 46, wherein:

the deformable region defines a cut through the fluid impermeable material of the cover;

the seal including fluid impermeable material is adhered to the cover over the cut; and the pad is adhered to the cover under the cut.

51. The apparatus of claim 46, wherein the pad is removeable and replaceable.

\*   \*   \*   \*   \*